United States Patent [19]
Olsson et al.

[11] Patent Number: 5,373,842
[45] Date of Patent: Dec. 20, 1994

[54] RESPIRATOR HAVING A TRIGGER SENSITIVITY DEPENDENT ON THE PATIENT GAS FLOW

[75] Inventors: Sven-Gunnar Olsson, Arloev; Goeran Rydgren, Bunkeflostrand; Dan Linden, Stockholm, all of Sweden

[73] Assignee: Siemens Aktiengesellschaft, Munich, Germany

[21] Appl. No.: 809,953

[22] Filed: Dec. 18, 1991

[30] Foreign Application Priority Data

Dec. 20, 1990 [XH] Hague Agreement ............ 90124930

[51] Int. Cl.$^5$ ...................... A61M 16/00; A62B 7/00; A62B 9/00; F16K 31/02
[52] U.S. Cl. ............................. 128/204.21; 128/204.28
[58] Field of Search ........................ 128/204.21, 204.25, 128/204.26, 205.23, DIG. 10

[56] References Cited

U.S. PATENT DOCUMENTS

| | | | |
|---|---|---|---|
| 3,033,195 | 5/1962 | Gilroy et al. | 128/204.21 |
| 3,741,208 | 6/1973 | Jonsson et al. | 128/202.22 |
| 3,765,239 | 10/1973 | Olsson | 128/205.23 |
| 3,961,627 | 6/1976 | Ernst et al. | 128/204.21 |
| 3,972,327 | 8/1976 | Ernst et al. | 128/204.21 |
| 4,323,064 | 4/1982 | Hoenig et al. | 128/204.21 |
| 4,401,116 | 8/1983 | Fry et al. | 128/205.24 |
| 5,148,802 | 9/1992 | Sanders et al. | 128/204.23 |
| 5,161,525 | 11/1992 | Kimm et al. | 128/204.23 |

FOREIGN PATENT DOCUMENTS 0046570  3/1982  European Pat. Off.
0402951 12/1990  European Pat. Off.
2596279 10/1987  France.

OTHER PUBLICATIONS

"Ventilators: Theory and Clinical Application", Dupuis, The C. V. Mosby Co., ©1986, St. Louis, MO., USA. pp. 17 & 18.
Instruction Manual for the Siemens Servo Ventilator 900 D, Oct., 1988.
Description for Option 50 ("Flow-by") for the Puritan-Bennett 7200a Ventilator, Oct., 1986.

Primary Examiner—Kimberly L. Asher
Attorney, Agent, or Firm—Hill, Steadman & Simpson

[57] ABSTRACT

A respirator has a bypass gas flow and respective valves in the inspiration and expiration lines for setting the gas flow through these lines. A control unit actuates the valves so that a respiratory cycle is produced and such that the bypass gas flow is maintained during expiration. The expiration pressure is identified by a pressure sensor. When this expiration pressure falls below a prescribed value, a new inspiration phase is triggered. To improve this triggering, the patient gas flow is identified by a flow meter, and the prescribed pressure value is varied dependent on the identified patient gas flow.

13 Claims, 2 Drawing Sheets

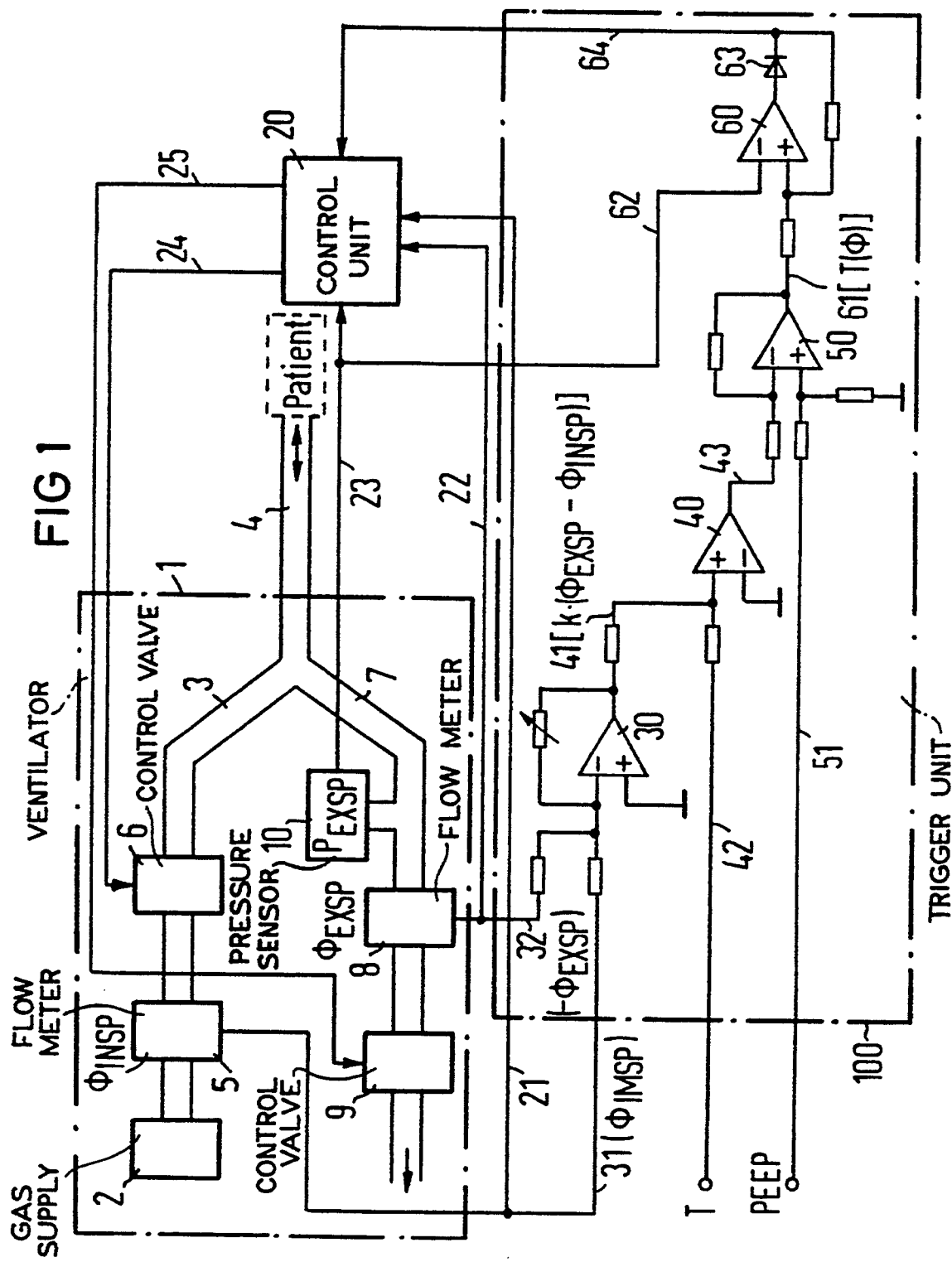

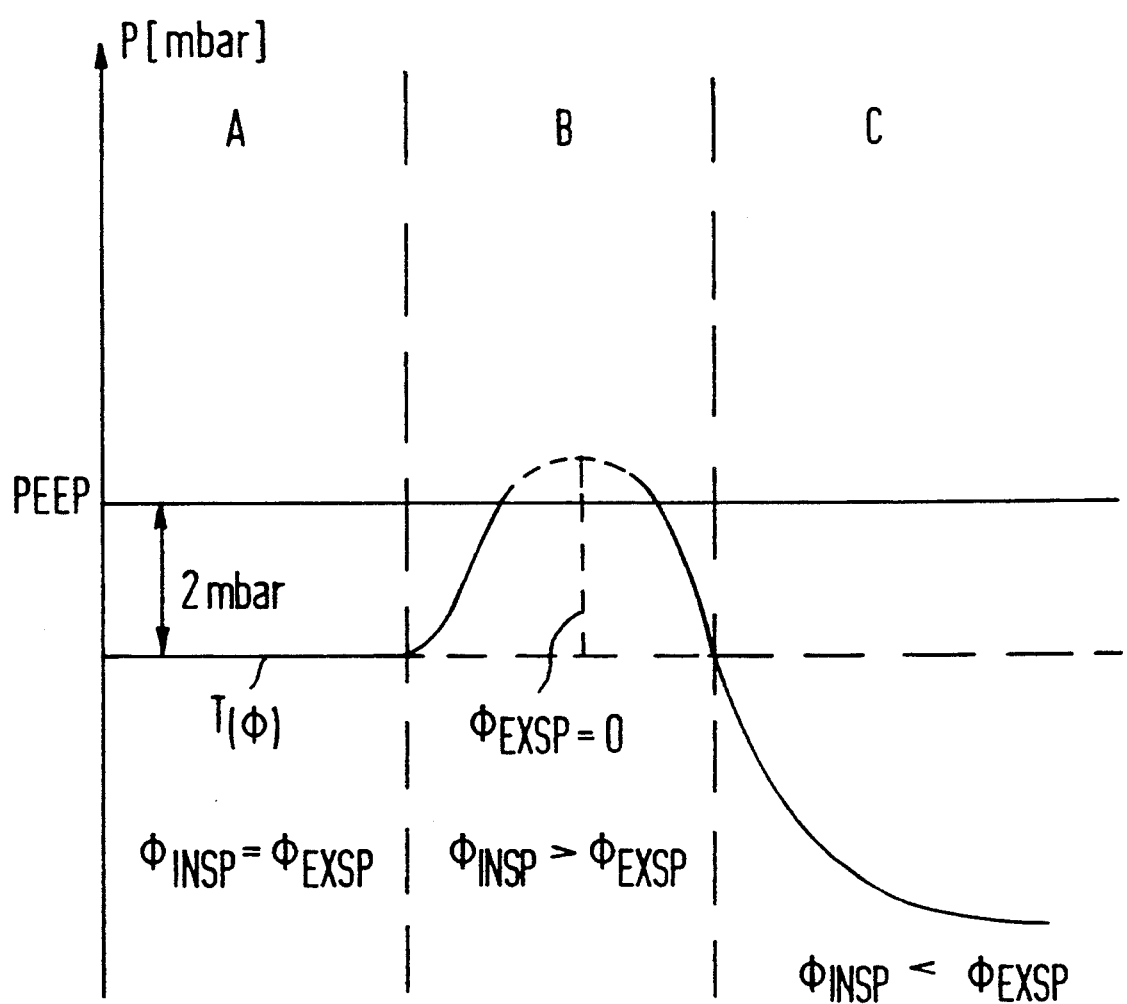

RESPIRATOR HAVING A TRIGGER SENSITIVITY DEPENDENT ON THE PATIENT GAS FLOW

BACKGROUND OF THE INVENTION

1. Field of the Invention

The present invention is directed to a respirator of the type wherein expiration pressure is identified by means of a pressure sensor, and a new inspiration phase is triggered when the expiration pressure falls below a prescribed value.

2. Description of the Prior Art

Respirators are known which include an inspiration line and an expiration line connectable to the respiratory paths of humans or animals, with the inspiration line having a first valve for setting the gas flow through the inspiration line, and the expiration line having a second valve for setting the gas flow through the expiration line. A control unit actuates the two valves in coordination so that a respiratory cycle having an inspiration phase and an expiration phase can be produced, the first valve remaining open to such an extent during the expiration phase that an adjustable bypass gas flow is produced. At least one pressure sensor identifies the expiration pressure and a trigger unit triggers a new inspiration phase during the course of the expiration phase when the pressure in the expiration line, as measured by the pressure sensor, falls below a prescribed value. A commercially available respirator is manufactured by Siemens known as Servo Ventilator 900 D (described in the Instruction Manual for the Servo Ventilator 900 D, Second German Edition, October 1988) which has an adjustable trigger level for the pressure in the expiration line. The trigger level is the relative underpressure which determines the pressure at which an inspiration shall be triggered. This pressure at which an inspiration is triggered is referred to as the trigger limit. The pressure in the expiration line is measured, and if the measured value falls below the trigger limit which has been set by virtue of, for example, a patient producing a corresponding underpressure due to an attempted inspiration, the respirator automatically switches from the expiration phase to the inspiration phase. In many instances, a positive end-expiration pressure (PEEP) is used during the expiration phase in order, for example, to prevent atelectasis. The PEEP range of adjustment, for example, may be from 0 through 50 mbar. The trigger level is thus dependent on the PEEP level. If, for example, a PEEP level of +10 mbar is selected and a trigger level of −2 mbar is selected, this means that a patient must produce an under pressure of 2 mbar, in comparison to the setting of the PEEP level, in order to trigger a breath. In other words, the trigger limit is +8 mbar.

The trigger level can be set to a fixed value by a rotary knob. Such setting can become difficult under certain circumstances. If the trigger level is set too low, i.e., if the spacing from the PEEP level to the trigger limit is selected too small, pressure fluctuations in the expiration line may cause (incorrectly) the triggering of a new breath, which should, of course, be avoided. Conversely, a trigger level which is too high, i.e., too large a spacing exists between the trigger limit and the PEEP level, can result in the patient having to exert a considerable force when attempting to breath, in order to generate the necessary underpressure in the expiration line. This is also undesirable. Due to the gas flow in the inspiration line which occurs even during the expiration phase, known as the bypass gas flow, the patient could initially inhale this gas quantity without the occurrence of a pressure drop in the expiration line.

The use of such a bypass gas flow is known, for example, from U.S. Pat. No. 4,401,116. The operation of a respirator with bypass gas flow is described in "Option 50" for the Model 7200a Ventilator manufactured by Puritan Bennett, Inc. This option is known as "flow-by". In contrast to the pressure-dependent triggering of a new breath described above, triggering dependent on gas flow is employed in this option. The gas flow in the inspiration line and in the expiration line is measured by means of two gas flow sensors, and a net gas flow is calculated therefrom. This corresponds to the patient gas flow, i.e., to the gas flow that is either absorbed when the patient inhales, or is expelled when the patient exhales. The net gas flow is zero during the respiratory pause, i.e., when the patient is neither inhaling nor exhaling.

When the patient begins to inhale, part of the bypass gas flow proceeds into the lungs of the patient, and the exhalation gas flow is correspondingly reduced. The net gas flow, or the patient gas flow, thus becomes negative. When this value reaches an adjustable sensitivity value, a new breath is triggered. For safety reasons, pressure-dependent triggering is always additionally provided as a back-up. These two trigger methods, which operate in parallel, make the setting and the manipulation of the ventilator even more complicated.

SUMMARY OF THE INVENTION

It is an object of the present invention to provide a ventilator of the type wherein respective valves in the inspiration and expiration lines are operated to produce a respiratory cycle and wherein triggering of a new breath occurs during the expiration phase, in which the triggering is improved and simplified.

The above object is achieved in accordance with the principles of the present invention in a ventilator wherein at least one flowmeter for calculating the patient gas flow is provided and wherein the prescribed value of pressure in the expiration line, which determines the point at which a new breath will be triggered (trigger limit), is varied dependent on the patient gas flow identified by this flow meter.

In contrast to known methods for triggering either in pressure-sensitive fashion or triggering dependent on the net gas flow through the respirator, a combination of these two trigger methods is disclosed herein, making the triggering more reliable and easier to use. The combination operates so that the trigger limit is varied by means of the patient gas flow, and thus the net gas flow, through the respirator. The trigger limit is moved towards the PEEP level (as is physiologically desired) when the net gas flow becomes negative, and thus the necessary underpressure for triggering a new breath becomes less.

In an embodiment of the invention, respective flow meters are provided in both the inspiration line and the expiration line, as are means for calculating the net gas flow therefrom. It is also possible to use only a single flow meter disposed immediately adjacent to the respiratory paths, or in a connecting line to the patient which is shared by the inspiration line and the expiration line. This single flow meter indicates both the magnitude and direction of the gas flow through the line.

In another embodiment of the invention, the maximum change of the trigger limit, which is reached when the total bypass gas flow is inhaled by the patient and the expiration flow thus becomes zero, is higher than the set trigger level. The trigger limit may therefore under these circumstances theoretically become higher than the PEEP level because the possible change in the trigger limit, due to changes in the net gas flow, is larger than the set trigger level. In practice, this means that a new inspiration starts when the trigger limit equals the PEEP level. In this case, triggering dependent on pressure becomes a quasi-triggering dependent on gas flow as the trigger limit varies with the net gas flow, when it is assumed that the pressure is correct, i.e., that (PEEP$-P_{EXSP}$)=0. The previously set, trigger level now determines, together with the patient gas flow, or net gas flow, at which pressure the triggering of a new breath occurs. Dependent on the strength of the inhalation by the patient, the trigger limit is displaced toward the PEEP level, and triggering ensues when trigger limit and the PEEP level are the same (i.e., when trigger limit and the pressure in the expiration line are the same). This technique has the advantage that the patient can initiate the triggering by inhaling the bypass gas flow, so that it is not necessary for the exertion associated with inhalation to be so large that an underpressure is produced in the expiration line. Conversely, the trigger limit, and thus the sensitivity, are lowered during exhalation by the patient, so that pressure fluctuations cannot produce false triggering, particularly at the start of the expiration phase.

If the trigger level is initially set lower than the possible, positive variation of the trigger limit, only pressure-dependent triggering is present, however, this triggering also has a sensitivity which is variable on the basis of the flow.

DESCRIPTION OF THE DRAWINGS

FIG. 1 is a schematic block diagram of a respirator constructed in accordance with the principles of the present invention.

FIG. 2 is a graph showing the dependency of the trigger level on different patient gas flows in the respirator of FIG. 1.

DESCRIPTION OF THE PREFERRED EMBODIMENTS

The portion of FIG. 1 indicated with reference symbol 1, bounded by dot-dash lines, is a ventilator of the type commercially available from Puritan Bennett, Inc. Only those components important for an explanation of the invention are schematically shown.

Gas is supplied via an inspiration line 3 from a gas supply 2 to a line 4 leading to a patient. A flow meter 5 and a control valve 6 for the gas flow, for example a solenoid valve, are disposed in the inspiration line 3.

An expiration line 7 is connected to the common line 4, and a further flow meter 8, a further control valve 9 and a pressure sensor 10 are disposed in the expiration line 7.

A control unit 20 is also shown in FIG. 1, with all functions of the respirator being capable of being controlled by the control unit 20 in a known manner, and the desired limit parameters are also set by means of the control unit 20. To this end, at least the values identified by the flow meters 5 and 8 and by the pressure sensor 10 are forwarded to the control unit 20 as electrical signals via respective lines 21, 22 and 23. The control valves 6 and 9 are operated by means of further lines 24 and 25. The control unit 20 may be analog unit. It is also possible to digitize the input signals, and to undertake the processing with a microprocessor.

An analog trigger unit 100, for triggering a new breath, is also shown in the exemplary embodiment of FIG. 1. The trigger unit 100 may, however, alternatively be a digital unit, with the individual measured values and the set values such as the trigger level or PEEP being digitized, and the triggering being calculated by a microprocessor.

The output signals from the flow meters 5 and 8 are supplied via respective lines 31 and 32 to a first amplifier 30 having a variable gain. The value $\Phi_{INSP}$ for the inspiration flow is supplied via the line 31, and the value for $-\Phi_{EXSP}$ for expiration flow is supplied via the line 32. A signal corresponding to the quantity $k(\Phi_{EXSP}-\Phi_{INSP})$ is thus present at the output line 41 of the amplifier 30, where k is the variable gain factor. A trigger level T which has been set, is added to this value in the amplifier 40, this trigger level T being supplied to the amplifier 40 via a line 42. The difference between a signal corresponding to the PEEP and the signal present at the output of the amplifier 40 on the line 43 is formed in a following differential amplifier 50. The signal corresponding to the PEEP is supplied to the positive input of the differential amplifier 50 via a line 51, and the output signal from the amplifier 40 is supplied to the negative input. A signal corresponding to the trigger limit dependent on the gas flow is thus present at the output line 61 of the differential amplifier 50. This signal is compared in a comparator 60 to the signal from the pressure sensor 10 in the expiration line, which is supplied to the comparator 60 via a line 62. When the expiration pressure is equal to the variable trigger limit or less, a trigger signal is forwarded to the control unit 20 via a diode 63 and a line 64, which causes the control unit 20 to generate a signal which closes the expiration valve 8 and opens the inspiration valve 6 in accord with the form of respiration which has been set, and thus initiating a new breath.

The resistors arranged in the various lines serve only the purpose of setting the correct gain and the correct operating points, and are therefore not set forth in greater detail.

This above-described evaluation circuit thus calculates the following value:

$$PEEP-[T+k(\Phi_{EXSP}-\Phi_{INSP})]-P_{EXSP}.$$

When this expression is greater than or equal to zero, a new breath is triggered. The gain factor k is selected such that the expression $k(\Phi_{EXSP}-\Phi_{INSP})$ corresponds to an increase in the variable trigger limit $T(\Phi)$ by a defined amount when the entire bypass gas is inhaled by the patient. This amount can be selected of a size such that it is greater than the spacing between PEEP and trigger limit, T for $\Phi_{EXSP}=\Phi_{INSP}$ i.e., the amount is greater than the trigger level.

The pressure conditions in the respirator of FIG. 1 are shown over time for various gas flows in FIG. 2. The PEEP is shown as the horizontal time axis. The PEEP level can be 0 mbar, or can be fixed to a variable value between zero and a few mbar. The trigger limit $T(\Phi)$ is dependent on the PEEP level. A set trigger level of $-2$ mbar, for example, corresponds to a lowering of the trigger limit by 2 mbar below the PEEP level, as indicated in the left third of FIG. 2. The trigger level is set as constant for this region A. In this region, the trigger limit is not influenced by the flow, since it is assumed that the inspiration flow is equal to the expiration flow and the net gas flow thus is zero. This constant trigger limit is also continued over the regions B and C as a dashed line. This limit would be valid if the aforementioned known, purely pressure-dependent triggering were used. The trigger limit would be defined by the manually set trigger level.

The middle region B of FIG. 2 indicates the trigger limit for that case wherein there is a net gas flow to the patient, i.e., the patient has spontaneously begun to inhale. As can be seen from this region of FIG. 2, the trigger limit approaches the PEEP level dependent on the size of this inhalation, and can theoretically even exceed the PEEP level, as indicated with dashed lines. The maximum value would be present when the expiration flow is zero, i.e., when the entire bypass gas is inhaled by the patient. Because, given correct pressure conditions, the pressure in the expiration line corresponds to the PEEP at least at the end of the expiration phase, a new breath is triggered when the trigger limit $T(\Phi)$ reaches the PEEP level. A triggering dependent on gas flow is thus present in this region. It is not necessary that the patient produce an underpressure with respect to the PEEP. The spontaneous initiation of a new breath is thus considerably facilitated for the patient, and is initiated considerably earlier than would be possible with a purely pressure-dependent triggering. In the case of purely pressure-dependent triggering, the patient would first have to inhale the entire bypass gas, and exert himself or herself to inhale even more gas before the pressure in the expiration line would drop below the PEEP level and down to the trigger limit shifted with respect thereto.

Section C of FIG. 2 shows the trigger limit for that case wherein the inspiration flow is lower than the expiration flow, i.e., when the patient is exhaling. The trigger limit is thereby moved farther from the PEEP level. The trigger sensitivity is thus diminished. This reliably prevents pressure fluctuations at the beginning of the exhalation phase from undesirably triggering a new breath.

The adjustable trigger sensitivity which corresponds to a net gas flow of zero can be increased such that the elevation of the trigger limit is not sufficient to reach the PEEP level, even given maximum inhalation of the entire bypass gas flow. Although a triggering dependent on gas flow is then no longer possible, the trigger limit for the necessary underpressure continues to be boosted, so that the pressure-dependent triggering becomes significantly more sensitive.

Although modifications and changes may be suggested by those skilled in the art, it is the intention of the inventors to embody within the patent warranted hereon all changes and modifications as reasonably and properly come within the scope of their contribution to the art.

We claim as our invention:

1. A respirator comprising:
   an inspiration line and an expiration line each adapted for connection to the respiratory path of a patient, and said inspiration line connected to a source of respiratory gas;
   first valve means disposed in said inspiration line for setting gas flow through said inspiration line;
   second valve means disposed in said expiration line for setting gas flow through said expiration line, said expiration line having a pressure therein;
   control means for operating said first and second valve means for producing a respiratory cycle having an inspiration phase and an expiration phase, including maintaining said first valve means open during said expiration phase to an extent for producing an adjustable bypass gas flow in said inspiration line;
   pressure sensor means for identifying the pressure in said expiration line;
   means for setting a pressure trigger limit;
   trigger means, connected to said pressure sensor means and to said control means, for triggering a new inspiration phase when the pressure, measured by said pressure sensor means, in said expiration line during said expiration phase falls below said pressure trigger limit;
   flow meter means, connected to said trigger means and to said control means, for identifying patient gas flow; and
   means in said control means for automatically changing said pressure trigger limit dependent on said patient gas flow identified by said flow meter means.

2. A respirator as claimed in claim 1 wherein said means for changing said pressure trigger limit dependent on said patient gas flow comprises means for lowering said pressure trigger limit when said patient gas flow is directed away from said patient and for raising said pressure trigger limit when said patient gas flow is directed toward said patient.

3. A respirator as claimed in claim 2 wherein said flow meter means comprises a first flow meter in said inspiration line and a second flow meter in said expiration line, and means connected to both said flow meters for calculating the patient gas flow as the net gas flow in said inspiration and expiration lines.

4. A respirator as claimed in claim 1 wherein said trigger means includes means for setting a selected pressure trigger level sensitivity, and wherein said means for changing said pressure trigger limit dependent on said patient gas flow comprises means for changing said pressure trigger limit dependent on a combination of said patient gas flow and said pressure trigger level sensitivity.

5. A respirator as claimed in claim 4 wherein said means for changing said pressure trigger limit includes means for setting a maximum, positive change in said pressure trigger limit to be greater than or equal to said trigger level when said gas flow through said inspiration line equals said gas flow through said expiration line.

6. A respirator as claimed in claim 1 wherein said pressure sensor means comprises means for generating an electrical signal corresponding to said pressure in said expiration line, wherein said flow meter means comprises means for generating an electrical signal corresponding to said patient gas flow in at least one of said inspiration line or said expiration line, and wherein said means for varying said pressure trigger limit comprises means for generating an electrical signal, supplied to said control means, corresponding to said pressure trigger limit.

7. A respirator as claimed in claim 6 wherein said pressure sensor means, said flow meter means and said means for varying said pressure trigger limit all comprise means for generating said respective electrical signals in the form of electrical voltages.

8. A respirator as claimed in claim 7 wherein said trigger means comprises:

means for setting a selected trigger level and for generating an electrical signal corresponding to said trigger level;

means for setting a selected PEEP value and for generating an electrical signal corresponding to said PEEP value;

a first amplifier having an input connected to receive said electrical signal from said flow meter means;

a second amplifier having an input connected to receive the output of said first amplifier and said electrical signal corresponding to said trigger level; and a differential amplifier having a first input connected to an output of said second amplifier and a second input connected to receive said electrical signal corresponding to said PEEP value, said differential amplifier having an output comprising said pressure trigger limit.

9. A respirator as claimed in claim 8 wherein said trigger means further comprises:

a comparator having a first input connected to receive said pressure trigger limit at the output of said differential amplifier and a second input connected to receive said electrical signal corresponding to said pressure in said expiration line, said comparator having an output connected to said control means for supplying a signal thereto for triggering said inspiration phase dependent on a comparison of said pressure trigger limit with said pressure in said expiration line.

10. A respirator as claimed in claim 8 wherein said first amplifier has a gain factor, and further comprising means for selectively varying said gain factor.

11. A method for operating a respirator having an inspiration line and an expiration line each adapted for connection to the respiratory path of a patient, and said inspiration line connected to a source of respiratory gas, said method comprising the steps of:

providing a first value disposed in said inspiration line and a second valve disposed in said expiration line;

setting gas flow through said inspiration line by operating said first valve disposed in said inspiration line; setting gas flow through said expiration line by operating said second valve disposed in said expiration line;

operating said first and second valves to produce a respiratory cycle having an inspiration phase and an expiration phase and maintaining said first valve open during said expiration phase to an extent for producing an adjustable bypass gas flow in said inspiration line;

providing a pressure sensor in said expiration line and sensing the pressure in said expiration line using said pressure sensor;

setting a pressure trigger limit;

triggering a new inspiration phase when the pressure sensed in said expiration line by said pressure sensor during said expiration phase falls below said pressure trigger limit;

identifying patient gas flow; and automatically changing said pressure trigger limit dependent on said patient gas flow.

12. A method as claimed in claim 11 wherein the step of changing said pressure trigger limit is further defined by decreasing said pressure trigger limit when said patient gas flow is directed away from said patient and increasing said pressure trigger limit when said patient gas flow is directed toward said patient.

13. A method as claimed in claim 11 wherein the step of triggering said inspiration phase is further defined by triggering said inspiration phase with an adjustable trigger level, and comprising the additional step of:

setting a maximum, positive change of said pressure trigger limit to be greater than or equal to said trigger level when said gas flow through said inspiration line equals said gas flow through said expiration line.

* * * * *